United States Patent

Leitner et al.

[11] Patent Number: 5,462,914
[45] Date of Patent: Oct. 31, 1995

[54] HERBICIDAL N-CYANOPYRIDAZINONES

[75] Inventors: Harald Leitner, Oftering; Rudolf H. Wörther, Linz; Horst Korntner, Linz; Rudolf Schneider, Linz; Engelbert Auer; Dietmar Kores, both of Leonding; Hermann Tramberger, Seitenstetten, all of Austria

[73] Assignee: Sandoz Ltd., Basel, Switzerland

[21] Appl. No.: 221,464

[22] Filed: Apr. 1, 1994

Related U.S. Application Data

[63] Continuation-in-part of Ser. No. 11,900, Feb. 1, 1993, abandoned.

[30] Foreign Application Priority Data

Feb. 17, 1992 [AT] Austria ........................................ 258/92

[51] Int. Cl.$^6$ .................................................. A01N 43/58
[52] U.S. Cl. ........................ 504/238; 544/239; 544/240
[58] Field of Search ................................. 544/239, 240; 504/236, 238

[56] References Cited

U.S. PATENT DOCUMENTS

| | | | |
|---|---|---|---|
| 2,741,615 | 4/1956 | Clark et al. | 546/44 |
| 3,886,155 | 5/1975 | Discus et al. | 504/238 |
| 3,967,952 | 7/1976 | Abdulla et al. | 504/238 |
| 4,013,658 | 3/1977 | Abdulla et al. | 504/238 |
| 4,058,390 | 11/1977 | Schönbeck et al. | 504/238 |
| 4,732,603 | 3/1988 | Patterson | 544/239 |
| 5,100,460 | 3/1992 | Desbordes et al. | 504/326 |
| 5,362,708 | 11/1994 | Kores et al. | 504/238 |

FOREIGN PATENT DOCUMENTS

| | | | |
|---|---|---|---|
| 237962 | 1/1965 | Austria. | |
| 4013734 | 10/1991 | Germany. | |
| 91798 | 10/1991 | Ireland. | |
| 0264575 | 11/1988 | Japan | 544/239 |

*Primary Examiner*—Donald G. Daus
*Attorney, Agent, or Firm*—Wenderoth, Lind & Ponack

[57] ABSTRACT

Novel herbicidal N-cyanopyridazinones of the general formula

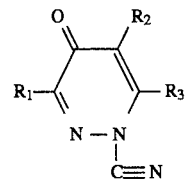

in which the radicals $R_1$, $R_2$ and $R_3$ independently of one another denote hydrogen, halogen, amino, nitro, cyano, alkyl, aryl, aralkyl, alkoxy or aryloxy groups, a process for their preparation, a herbicidal composition comprising them, and a method of controlling weeds.

9 Claims, No Drawings

HERBICIDAL N-CYANOPYRIDAZINONES

This application is a Continuation-in-Part of now abandoned application, Ser. No. 08/011,900, filed Feb. 1, 1993, abandoned.

The invention relates to novel herbicidally active N-cyanopyridazinones, to a process for their preparation, to herbicidal compositions comprising the novel N-cyanopyridazinones, to a process for their preparation, and to a method of controlling weeds.

U.S. Pat. No. 3,967,952 and U.S. Pat. No. 4,013,658 disclose herbicidal 3,5-diphen-yl- 4(1H)-pyridazinones and -pyridazinethiones which are substituted on the 1-nitrogen by alkyl groups having 1 to 3 C atoms. However, the application rate required for a herbicidal action is exorbitantly high.

Unexpectedly, novel N-cyanopyridazin-4-ones which have an outstanding herbicidal activity even when used at low application rates have now been found.

The invention therefore relates to N-cyanopyridazinones of the general formula

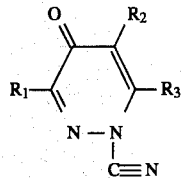

in which $R_2$ denotes hydrogen, Cl or Br, $R_1$ and $R_3$ are the same and each denote Cl, Br or I or $R_1$ or $R_3$ denote Cl, Br, I, alkoxy having 1 or 8 carbon atoms, phenyl, which is unsubstituted or mono- or polysubstituted by hydroxyl, halogen, cyano, nitro, amino, alkylamino having 1–4 C atoms, dialkylamino, each alkyl having 1–4 C atoms, straight-chain or branched alkyl having 1–10 C atoms being unsubstituted or mono or polysubstituted by halogen or cyano, straight-chain or branched alkoxy having 1–10 C atoms, cycloalkyl having 5–7 C atoms, cycloalkoxy having 5–7 C atoms, phenyl, phenoxy, alkylthio or alkylsulfonyl having 1–4 C atoms.

The invention also relates to a process for the preparation of N-cyanopyridazinones of the general formula

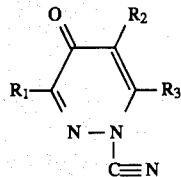

in which $R_2$ denotes hydrogen Cl or Br, $R_1$ and $R_3$ are the same and each denote Cl, Br or I or $R_1$ or $R_3$ denote Cl, Br I, alkoxy having 1 to 8 carbon atoms, phenyl, which is unsubstituted or mono- or polysubstituted by hydroxyl, halogen, cyano, nitro, amino, alkylamino having 1–4 C atoms, dialkylamino, each alkyl having 1–4 C atoms, straight-chain or branched alkyl having 1–10 C atoms being unsubstituted or mono or polysubstituted by halogen or cyano, straight-chain or branched alkoxy having 1–10 C atoms, cycloalkyl having 5–7 C atoms, cycloalkoxy having 5–7 C atoms, phenyl, phenoxy, alkylthio or alkylsulfonyl having 1–4 C atoms, which comprises:

reacting a hydroxypyridazine of the formula

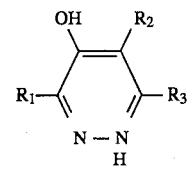

in which $R_1$, $R_2$ and $R_3$ have the above meaning, dissolved or suspended in a diluent, which is inert reaction conditions, with an inorganic or organic base to yield the corresponding salt, reacting the salt with a cyanogen halide and isolating the N-cyanopyridazinone from the reaction mixture.

To prepare the compounds of the general formula I, the hydroxypyridazine of the general formula II, dissolved or suspended in a diluent which is inert under the reaction conditions, for example chlorinated hydrocarbons such as methylene chloride, ethylene chloride, trichloroethylene, ketones such as acetone, dibutyl ketone, ethers such as diisopropyl ether, dioxane, acid amides such as dimethylformamide, dialkyl sulfoxides such as dimethyl sulfoxide, alcohols such as methanol, ethanol, diisopropyl alcohol, water or mixtures of the abovementioned diluents, can be reacted with an inorganic or organic base, for example sodium hydroxide, sodium hydride, sodium carbonate, potassium hydroxide, potassium hydride or potassium carbonate, ammonia, amines such as triethylamine, pyridine, preferably with amines, particularly preferably with triethylamine, and with a cyanogen halide such as cyanogen chloride, cyanogen bromide or cyanogen iodide, preferably cyanogen chloride or cyanogen bromide. What is unusual is that the reaction also proceeds in water or in aqueous mixtures of organic diluents.

In general, the cyanogen halide and the base are employed in at least equimolar amounts or in an excess relative to the hydroxypyridazine of the formula II, but in some cases it can also be advantageous to employ an excess of the hydroxypyridazine of the formula II. The base and the cyanogen halide are added at temperatures from approximately −70° C. to the boiling point of the diluent used, depending on the chemical structure of the reactants used. It is preferred to add the base and the cyanogen halide at temperatures from −10° C. to 60° C., especially preferably from approximately 0° C. to room temperature. The temperature of the reaction mixture generally rises as the cyanogen halide is added. When the addition, which may optionally be carried out with cooling, has ended, the mixture can be left to react further at a given temperature, or the reaction mixture is heated to complete the reaction, if appropriate up to the boiling point of the diluent used. In general, however, heating is not required. It is preferred to add the base and the cyanogen halide at room temperature and to allow the reaction to take place at the resulting temperature, without external cooling or heating.

In contrast to acyl halides, the cyanogen halide does not react with the oxygen atom in the 4-position, but, unexpectedly, with the nitrogen atom in the 1-position of the pyridazine ring.

The reaction can be monitored in the customary manner, for example by chromatography. When the reaction has ended, the salt formed from the halogen of the cyanogen halide with the base is removed from the reaction mixture in a conventional manner, for example by filtration or extraction, whereupon the organic diluent is evaporated. The desired N-cyanopyridazinone of the general formula I remains as an oily or crystalline residue. If desired, the residue can be subjected to a further purification step, for example chromatography or recrystallization.

In the case of compounds of the formula I in which $R_1$ is an aryl group and $R_3$ is a halogen group, it has emerged that the 6-position, in which $R_3$ is bonded, is particularly reactive, so that $R_3$ can be replaced by other functional groups. For example, the chlorine atom in the compound 1-cyano-3-phenyl-6-chloropyridazin-4-one can be converted into the compound 1-cyano-3-phenyl-6-iodopyridazin- 4-one by reacting it with sodium iodide in an organic solvent. This means that it is also possible to obtain compounds of the formula I from compounds of the formula I by substituting a functional group in the 6-position of the pyridazinone ring with another functional group.

The preparation of the starting compounds of the general formula II is known, for example, from DE 4,013,734 and can be carried out for example by reacting suitable pyridazines with an alkali metal hydroxide or by dealkylation of a 4-alkoxypyridazine, for example with the aid of alkali metal hydride and alkanethiol, in a diluent which is inert under the reaction conditions.

For example, 3-aryl-4-hydroxy-6-bromopyridazine can be prepared by reacting 3-aryl-4,6-dibromopyridazine with sodium hydroxide in dioxane/water, and 3-phenyl-4-hydroxy- 6-methoxypyridazine can be prepared from 4,6-dimethoxy- 3-phenylpyridazine by reacting it with sodium hydride and butanethiol in dimethylformamide.

3-Arylalkoxypyridazines can be prepared, for example, from the corresponding 3-arylhalopyridazines by reacting them with alkali metal alcoholate. 3-Arylhalopyridazines such as, for example, 3-(3'-trifluoromethylphenyl)-4,6-dichloropyridazine, can be prepared for example from 3-arylpyridazin- 6-one by halogenation in phosphorus oxychloride using red phosphorus and elemental halogen. A longer halogenation time allows all positions 4, 5 and 6 of the pyridazinone ring to be halogenated stepwise.

The N-cyanopyridazinones according to the invention have an outstanding herbicidal action and represent therefore an enrichment of the art. They are suitable for controlling dicotyledon, but also monocotyledon, seed-propagated weeds in crops such as cereals, maize, ground-nut, brassicas, chickpeas, tomatoes and onions.

They are particularly suitable for controlling, for example,
Amaranthus retroflexus (AMARE)—redroot
Anthemis arvensis (ANTAR)—corn chamomile
Centaurea cyanus (CENCY)—cornflower
Chenopodium album (CHEAL)—pigweed
Echinochloa crus-galli (ECHCG)—common barnyard grass
Galium aparine (GALAP)—catchweed bedstraw
Lapsana communis (LAPCO)—nipplewort
Stellaria media (STEME)—common chickweed in the abovementioned crops.

The invention also relates to a herbicidal composition which comprises, besides additives and/or carriers, at least one N-cyanopyridazinone of the general formula I according to claim 1.

The herbicidal composition is formulated in a known manner, for example by mixing the active ingredients with extenders, i.e. liquid solvents, liquefied gases under pressure and/or solid carriers, optionally using surfactants, i.e. emulsifiers and/or dispersants and/or wetting agents and/or foam-forming agents. If water is used as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as methylene chloride, trichlorbenzeneso aliphatics such as cyclohexane or paraffins, for example mineral oil fractions, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulfoxide, and also water. Liquefied gaseous extenders or carriers are to be understood as meaning those liquids which are gaseous at normal temperature and under atmospheric pressure, for example aerosol propellent such as halohydrocarbons as well as butane, propane, nitrogen and carbon dioxide; the following are suitable as solid carriers: for example natural ground rocks such as kaolins, clays, talc, chalk, quartz, attapulgite, montmorillonite or diatomaceous earth, and synthetic products such as highly disperse silica, alumina and silicates; the following are suitable as solid carriers for granules: for example crushed and fractionated natural rocks such as calcite, marble, pumice, sepiolite, dolomite as well as synthetic granules of inorganic and organic meals, as well as granules of organic material such as sawdust, coconut shells, maize cobs and tobacco stalks; the following are suitable as emulsifiers and/or foam-forming agents: for example non-ionic and ionic surfactants such as polyoxyethylene sorbitan tall oil esters, sodium oleylmethyltauride, polyoxyethylene fatty acid esters, polyoxyethylene fatty alcohol ethers, for example alkylaryl polyglycol ethers, alkylsulfonates, alkyl sulfates, aryl sulfates and arylalkylsulfonates, as well as protein hydrolyzates. Examples of wetting agents which can be employed are polyoxethylated alkylphenols, polyoxethylated oleylamines or stearylamines, alkylsulfonates or alkylphenylsulfonates. The following are suitable as dispersants: for example ligninsulfonates, or condensation products of arylsulfonates with formaldehyde.

Adhesives and thickeners such as carboxymethylcellulose, methylcellulose, natural and synthetic polymers in the form of powders, granules and latices, such as gum arabic, polyvinyl alcohol or polyvinyl acetate, can be used in the formulations.

Colorants such as inorganic pigments, for example iron oxide, titanium oxide, Prussian Blue, and organic dyestuffs such as alizarin, azo and metal phthalocyanine dyestuffs, and trace nutrients such as salts of iron, manganese, boron, copper, cobalt, molybdenum and zinc, can be used.

In general, the formulations comprise between 0.1 and 95% by weight of active ingredient, preferably between 0.5 and 90% by weight.

The active ingredients can be applied as such, in the form of their formulations or in the use forms prepared therefrom by further dilution, such as ready-to-use solutions, emulsions, suspensions, powders, pastes and granules. Wettable powders are preparations which are uniformly dispersible in water and which can additionally comprise wetting agents besides the active ingredients and, if appropriate, in addition to diluents or inert substances. Emulsifiable concentrates can be prepared for example by dissolving the active ingredients in an organic solvent with addition of one or more emulsifiers. Dusts are obtained by grinding the active ingredients with finely divided solid carriers.

They are used in the customary manner, for example by pouring, immersing, spraying, atomizing, fogging, vaporizing, injecting, forming a slurry, dusting, scattering, dry seed treatment, damp seed treatment, wet seed treatment, slurry treatment or incrusting.

The rate at which the compositions according to the invention are to be applied varies with the external conditions such as, inter alia, temperature and humidity. It can vary within wide limits and is generally between 0.1 and 5 kg of active ingredient/ha, preferably 0.1 to 1.7 kg/ha.

EXAMPLE 1

10.35 g of 3-phenyl-4-hydroxy-6-chloropyridazine (0.05 mol) were suspended in 100 ml of acetone, and 6.07 g of triethylamine (0.06 mol) were added at room temperature with stirring. After approximately half an hour, 6.36 g of cyanogen bromide (0.06 mol), dissolved in acetone, were added dropwise to the reaction mixture, during which process the temperature of the reaction mixture rose slightly. After stirring overnight, the triethylammonium bromide which had precipitated was filtered off, and the organic solvent was evaporated. The crystallizing residue was digested in 100 ml of water, filtered, washed with water and dried.

This gave 11.3 g of 1-cyano-3-phenyl-6-chloropyridazin-4-one, which is 97% of theory. After recrystallization from diisopropyl ether/acetone =7:3, white crystals having a melting point of 120° to 121° C. were obtained.

A similar result was obtained when 5.3 g of cyanogen bromide (0.05 mol) were used under otherwise identical conditions.

EXAMPLE 2

12.55 g of 3-phenyl-4-hydroxy-6-bromopyridazine (0.05 mol) were suspended in 100 ml of acetone, and 7.6 g of triethylamine (0.075 mol) were added at room temperature with stirring. After half an hour of stirring, 10.6 g of cyanogen bromide (0.1 mol), dissolved in 100 ml of acetone, were added dropwise, during which process the temperature rose slightly. After stirring overnight, precipitated triethylammonium bromide was filtered off, arid the organic solvent was evaporated. The residue was digested in 100 ml of water, and the solid obtained was filtered off, washed with water and dried.

This gave 12.6 g of 1-cyano-3-phenyl-6-bromo-pyridazin-4-one, which is 91% of theory.

To purify the product further, it was chromatographed over a silica gel column using chloroform as the eluent and subsequently recrystallized from an acetone/-diisopropyl ether mixture, which gave white crystals having a melting point of 152° to 155° C.

EXAMPLE 3

413.3 g of 3-phenyl-4-hydroxy-6-chloropyridazine (2.0 mol) were dissolved in a solution of 80 g of sodium hydroxide in 1.6 l of water, and 1.6 l of acetone were added. 211.9 g of cyanogen bromide (2.0 mol) were added to this solution at 25° C. During this process, the temperature rose to 31° C. and the pH dropped from 9 to 6. After stirring at room temperature for 2 hours, the solid which had precipitated was filtered off with suction, washed with aqueous acetone and dried.
This gave 425 g of 1-cyano-3-phenyl-6-chloropyridazin-4-one in a yield of 92% of theory. After the product had been stirred in a 5% strength aqueous NaHCO$_3$ solution, washed with water and dried, a melting point of 117°–120° C. was measured.

EXAMPLE 4

At −3° to 0° C., 56.7 g of chlorine gas were passed into a solution of 10.8 g of sodium chloride and 1.7 ml of concentrated hydrochloric acid in 577 ml of water, and 217.7 ml of a 30% by weight solution of sodium cyanide in water were introduced, giving an aqueous solution of cyanogen chloride.

At −5° C., a solution of 82.6 g of 3-phenyl-4-hydroxy-6-chloropyridazine (0.4 mol) and 16 g of sodium hydroxide in 417 ml of water and 667 ml of acetone were added to this solution. After the mixture had been stirred for 4 hours at room temperature, the precipitate formed was filtered off with suction, washed with water and dried. This gave 90 g of 1-cyano-3-phenyl-6-chloropyridazin-4-one, which is 97% of theory, having a melting point of 117° to 119° C.

EXAMPLE 5

This was carried out as described for Example 4 but using dioxane/water in place of acetone/water. This gave 96% of theory of 1-cyano-3-phenyl-6-chloropyridazin- 4-one having a melting point of 120° to 121° C.

EXAMPLE 6

This was carried out as described in Example 4 but using water without addition of acetone as the solvent. This gave 97% of theory of 1-cyano-3-phenyl-6-chloropyridazin-4-one having a melting point of 117° to 119° C.

The compounds listed in Table 1 were obtained in the manner described for Examples 1 to 6 using suitable starting materials.

TABLE 1

|    | $R_1$           | $R_2$ | $R_3$      | M.p. (°C.) |
|----|-----------------|-------|------------|------------|
| 7  | Cl              | H     | Cl         | 167–169    |
| 8  | phenyl          | H     | OCH$_3$    | 185–190    |
| 9  | phenyl          | H     | OC$_4$H$_9$ | 162–164   |
| 10 | phenyl          | H     | Cl         | 145–146    |
| 11 | 4-Br-phenyl     | H     | Cl         | 122–123    |
| 12 | 2-F-phenyl      | H     | Cl         | 157–159    |
| 13 | 3Cl,4Cl-phenyl  | H     | Cl         | 153–157    |
| 14 | 2Cl,3Cl,4Cl-phenyl | H  | Cl         | 180–184    |
| 15 | 4-CN-phenyl     | H     | Cl         | 204–208    |
| 16 | 4-NO$_2$-phenyl | H     | Cl         | 205–209    |
| 17 | 4-C$_2$H$_5$-phenyl | H | Cl         | 97–98      |
| 18 | 3-CF$_3$-phenyl | H     | Cl         | 74–77      |
| 19 | 4-OCH$_3$-phenyl | H    | Cl         | 153–155    |
| 20 | 4-F-phenyl      | Cl    | Cl         | 138–140    |
| 21 | 3Cl,4Cl-phenyl  | Cl    | Cl         | 162–165    |
| 22 | Cl              | Cl    | phenyl     | 170–173    |
| 23 | Cl              | Cl    | 3-Br-phenyl | 196–200   |

EXAMPLE 24

87.5 g of 1-cyano-3-phenyl-6-chloropyridazin-4-one (0.378 mol) and 136 g of sodium iodide were dissolved in 700 ml of acetone, and the solution was refluxed for 88 hours. The solvent was then evaporated and the residue triturated with water. The solid formed in this process was filtered off and dried.
This gave 116 g of 1-cyano-3-phenyl-6-iodopyridazin-4-one, which is 95% of theory.
After purification by means of column chromatography (SiO$_2$, CHCl$_3$) and subsequent recrystallization from diisopropyl ether: acetone 7:3, a melting point of 135° to 137° C. was measured.

EXAMPLE 25

A solution of 85.8 g of phosphorus oxybromide (0.3 mol) in 150 ml of toluene was added, at room temperature and with stirring, to 20.6 g of 3-phenyl-4-hydroxy- 6-chloropyridazine (0.1 mol), whereupon the mixture was refluxed for 3 hours. During this process, hydrogen bromide gas was formed and stripped off. When the reaction had ended, the reaction mixture was poured onto ice, giving a pasty reaction product which solidified upon trituration in petroleum ether. The solid was filtered off, washed with water and dried.

This gave 27.1 g of 3-phenyl-4,6-dibromopyridazine, which is 88% of theory, having a melting point of 145°–146° C.

EXAMPLE 26

47.0 g of 3-phenyl-4,6-dibromopyridazine (0.15 mol) were refluxed in 300 ml of dioxane and treated in the course of 10 minutes with 17 g of sodium hydroxide (0.43 mol) dissolved in 50 ml of water. After 4.5 hours at reflux temperature, the dioxane was evaporated, and the solid residue was dissolved in hot water. After a tar-like residue had been filtered off with the aid of active charcoal, hydrochloric acid was added until the reaction was clearly acidic, during which process a solid precipitated. The solid was filtered off, made into a slurry with water and dissolved by adding aqueous ammonia while heating. The solid was reprecipitated by renewed acidification with hydrochloric acid, filtered off, washed with water and dried.

This gave 24.2 g of 3-phenyl-4-hydroxy-6-bromopyridazine, which is 64% of theory, having a melting point of 210° to 215° C.

EXAMPLE 27

96.1 g of 3-(3'-trifluoromethylphenyl)pyridazin 6-one were suspended in 400 ml of phosphorus oxychloride and treated with 12.4 g of red phosphorus. Chlorine gas was slowly passed into the suspension, during which process the temperature rose and was then kept at approximately 95° C. by external heating of the reaction mixture. The reaction was complete after 1.75 hours. The reaction mixture was cooled to room temperature and poured onto ice, during which process the acid which had formed was neutralized by a simultaneous addition of aqueous ammonia. The solid obtained was filtered off, dried and recrystallized from hexane.

This gave 84.4 g of 3-(3'-trifluoromethylphenyl) 4,6-dichloropyridazine, which is 72% of theory, having a melting point of 80° to 81.5° C.

EXAMPLE 28–32

Using suitable starting materials,
28. 3-(4'-bromophenyl)-4,6-dichloropyridazine having a melting point of 170° to 171° C.,
29. 3-(3',4'-dichlorophenyl)-4,6-dichloropyridazine having a melting point of 153° to 154.5° C.
30. 3-(2'-fluorophenyl)-4,6-dichloropyridazine having a melting point of 96° to 98° C.,
31. 3-(4'-cyanophenyl)-4,6-dichloropyridazine having a melting point of 210° to 222° C. and
32. 3-(4'-ethylphenyl)-4,6-dichloropyridazine having a melting point of 35° to 39° C.
were obtained in the manner described in Example 16.

EXAMPLE 33

70 g of 3-phenylpyridazin-6-one (0.41 mol) and 10 g of red phosphorus were suspended in 300 ml of phosphorus oxychloride. Chlorine gas was passed into this suspension with stirring, the reaction temperature, which first rose during this process, being kept at temperatures from 70° to 75° C., first by cooling and then by heating the reaction mixture. After 3 hours, the reaction mixture was allowed to cool to room temperature and poured onto ice, and the acid formed was neutralized by addition of aqueous ammonia. The solid obtained was filtered off, washed with water and then recrystallized twice from ethanol.

88.9 g of 3,4,5-trichloro-6-phenylpyridazine, which is 84% of theory, having a melting point of 120° to 121.5° C. were obtained.

EXAMPLES 34–36

Using suitable starting materials,
34. 3,4,5-trichloro-6-(4'-bromophenyl)pyridazine having a melting point of 164° to 167° C.,
35. 3,4,5-trichloro-6-(4'-chlorophenyl)pyridazine having a melting point of 155° to 159° C. and
36. 3,4,5-trichloro-6-(4'-fluorophenyl)pyridazine having a melting point of 153° to 155° C.
were obtained in the manner described in Example 22.

EXAMPLE 37

75 g of 3,4,5-trichloro-6-(4'-chlorophenyl)pyridazine (0.255 mol) were dissolved in 300 ml of dioxane at boiling point, and 100 ml of water were added. A solution of 20.4 g of sodium hydroxide in 150 ml of water was added dropwise to this solution in the course of 30 minutes. The solvent was evaporated, and the residue was dissolved in hot water. By adding aqueous hydrochloric acid, a solid was precipitated which was filtered off and reprecipitated for purification by dissolving in a dilute aqueous ammonia solution followed by an addition of hydrochloric acid. The solid was filtered off and recrystallized from an ethanol/dimethyl sulfoxide mixture, giving 36.6 g of 3,5-dichloro-4-hydroxy-6-(4'-chlorophenyl)pyridazine, which is 52% of theory, having a melting point of 272° to 278° C. (decomposition).

EXAMPLES 38–40

Using suitable starting materials,
38. 3,5-dichloro-4-hydroxy-6-phenylpyridazine having a melting point of 190° to 193° C.,
39. 3,5-dichloro-4-hydroxy-6-(4'-fluorophenyl)pyridazine having a melting point of 266° to 270° C. and
40. 3,5-dichloro-4-hydroxy-6-(4'-bromophenyl)pyridazine having a melting point of 276° to 281° C.
were prepared in the manner described in Example 26.

EXAMPLE 41

45 g of 3-phenyl-4,6-dichloropyridazine (0.2 mol) were dissolved in 600 ml of methanol, and 108 g of a 30% strength solution of sodium methylate in methanol (0.6 mol) were added, whereupon the reaction mixture was refluxed for 7 hours. After the reaction mixture had been cooled, the precipitated sodium chloride was filtered off and the organic phase was evaporated. The residue was taken up in methylene chloride/water, and the organic phase was extracted by shaking with water, dried over sodium sulfate and evaporated. The residue was recrystallized from cyclohexane.

This gave 39.9 g of 3-phenyl-4,6-dimethoxypyridazine, which is 92% of theory, having a melting point of 53° to 54° C.

EXAMPLE 42

4,6-Dibutoxy-3-phenylpyridazine was obtained in the form of a pale, chlorine-free oil in the manner described for Example 41, but using sodium butylate in place of sodium methylate.

EXAMPLE 43

39.9 g of 3-phenyl-4,6-dimethoxypyridazine (0.18 mol) were dissolved in 500 ml of dimethylformamide, and 4.9 g of an 80 % suspension of sodium hydride in mineral oil were added at room temperature. 18.4 g of butanethiol (0.2 mol) were subsequently added dropwise to the reaction mixture, during which process the temperature rose slightly. After the mixture had been stirred at room temperature for a few hours, it was heated for 5 hours at 100° C., whereupon the solvent was evaporated. The residue was taken up in water/ cyclohexane, and the aqueous phase was extracted by shaking with cyclohexane and acidified by adding acetic acid, during which process a solid precipitated which was filtered off, washed with water and dried. This gave 32.5 g of 3-phenyl-4-hydroxy 6-methoxypyridazine, which is 87% of theory, having a melting point of 204° to 209° C. after recrystallization from a mixture of methanol: dimethylformamide =1:1.

EXAMPLE 44

Starting from 3-phenyl-4,6-dibutoxypyridazine, 3-phenyl- 4-hydroxy-6-butoxypyridazine having a melting point of 217° to 220° C. was obtained in the manner described for Example 41.

EXAMPLE 45

0.5 part of compound 1 were mixed intimately with 5 parts of sodium N-oleyl-N-methyltauride, 3 parts of sodium diisobutylnaphthalenesulfonate, 10 parts of calcium ligninsulfonate and 81.5 parts of kaolin, and the mixture was subsequently ground for 1 hour in a planetary mill.
This gave a wettable powder which is suitable for the preparation of a herbicidal spray mixture.

EXAMPLE 46

10 parts of compound 1 were dissolved in 30 parts of xylene and 40 parts of N-methylpyrrolidone, and 10 parts of an emulsifier mixture composed of calcium dodecylbenzenesulfonate and ethoxylated tall oil fatty acid, were added. This gave an emulsifiable concentrate which is suitable for the preparation of a herbicidal spray mixture.

EXAMPLE 47

25 parts of compound 1 were intimately mixed with 5 parts of sodium N-oleyl-N-methyltauride, 3 parts of sodium diisobutylnaphthalenesulfonate, 10 parts of calcium ligninsulfonate, 25 parts of Attaclay$^R$ and 32 parts of kaolin, and the mixture was subsequently ground for one hour in a planetary mill.
This gave a wettable powder which is suitable for the preparation of a herbicidal spray mixture.

EXAMPLE 48

60 parts of compound 1 were intimately mixed with 5 parts of sodium N-oleyl-N-methyltauride, 3 parts of sodium lauryl sulfate, 10 parts of calcium ligninsulfonate and 22 parts of Attaclay$^R$, and the mixture was subsequently ground for one hour in a planetary mill.
This gave a wettable powder which is suitable for the preparation of a herbicidal spray mixture.

EXAMPLE 49

90 parts of compound 1 were intimately mixed with 4 parts of sodium N-oleyl-N-methyltauride, 2 parts of sodium diisobutylnaphthalenesulfonate and 4 parts of precipitated silica, and the mixture was subsequently ground for one hour in a planetary mill.
This gave a wettable powder which is suitable for the preparation of a herbicidal spray mixture.

To check the activity of the novel N-cyanopyridazinones, a certain amount of active substance was applied post-emergence to the test plants (3 to 6-leaf stage). The plants were scored 2 to 3 times. The values given are averages from all scorings. The results were evaluated by the key of the EWRC scale 1–9 given in Table 2.

TABLE 2

| Figure of merit | Herbicidal Action | Percentage |
| --- | --- | --- |
| 1 | excellent | 100 |
| 2 | very good | > 97.5 |
| 3 | good | > 95.0 |
| 4 | satisfactory | > 90.0 |
| 5 | acceptable | > 85.0 |
| 6 | not acceptable | < 85.0 |
| 7 | poor | < 75.0 |
| 8 | very poor | < 65.0 |
| 9 | no action | < 32.5 |

The comparison substance used was the known herbicide Lentagran, manufactured by Chemie Linz AG (6-chloro-3-phenylpyridazin-4-yl S-octyl thiocarbonate). The dosage rate is indicated in grams of active substance per hectare. In some cases the preparations were applied together with Nopon 11E. NOPON 11E is a commercial preparation manufactured by Sun Oil and is composed of 99% paraffin oil and one percent emulsifiers.

EXAMPLE A

| | | Herbicidal Action | | |
| --- | --- | --- | --- | --- |
| Preparation | Dosage Rate | STEME | LAPCO | ANTAR |
| Lentagran | 250 | 8.0 | 5.5 | 7.0 |
| Compound 1 | 250 | 6.5 | 2.0 | 1.0 |

EXAMPLE B

The active substances were applied in each case together with 5.0 liters of NOPON 11E per hectare.

| | | Herbicidal Action in % |
| --- | --- | --- |
| Preparation | Dosage Rate | ECHCG |
| Lentagran | 600 | 78 |
| Lentagran | 450 | 38 |
| Compound 1 | 367 | 78 |
| Compound 1 | 275 | 56 |
| Compound 2 | 437 | 75 |
| Compound 2 | 327 | 58 |
| Compound 15 | 406 | 69 |
| Compound 15 | 304 | 66 |

EXAMPLE C

The active substances were applied in each case together with 2.5 liters of NOPON 11E per hectare.

| Preparation | Dosage Rate | Herbicidal Action | |
| --- | --- | --- | --- |
| | | CHEAL | AMARE |
| Lentagran | 300 | 5.0 | 2.7 |
| Lentagran | 225 | 6.3 | 3.3 |
| Compound 1 | 183 | 4.0 | 2.7 |
| Compound 1 | 138 | 6.3 | 2.7 |
| Compound 2 | 218.4 | 2.3 | 2.0 |
| Compound 2 | 163.5 | 3.3 | 2.3 |
| Compound 11 | 246 | 1.3 | 2.3 |
| Compound 11 | 184 | 2.0 | 3.7 |
| Compound 13 | 238 | 1.3 | 2.0 |
| Compound 13 | 178 | 2.3 | 2.3 |
| Compound 15 | 203 | 1.3 | 2.0 |
| Compound 15 | 152 | 1.3 | 1.7 |

What we claim is:

1. N-cyanopyridazinones of the formula:

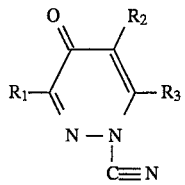

in which $R_2$ denotes hydrogen, Cl or Br, $R_1$ and $R_3$ are the same and each denote Cl, Br or I or $R_1$ or $R_3$ denote Cl, Br, I, alkoxy having 1 to 8 carbon atoms, phenyl, which is unsubstituted or mono- or disubstituted by hydroxyl, halogen, cyano, nitro, amino, alkylamino having 1–4 C atoms, dialkylamino, each alkyl having 1–4 C atoms, straight-chain or branched alkyl having 1–10 C atoms being unsubstituted or mono-substituted by cyano or mono to trisubstituted by halogen; cycloalkyl having 5–7 C atoms, cycloalkoxy having 5–7 C atoms, phenyl, phenoxy, alkylthio or alkylsulfonyl having 1–4 C atoms; or trisubstituted by chlorine.

2. N-cyanopyridazinones according to claim 1, in which $R_2$ denotes hydrogen and $R_1$ or $R_3$ denote halogen or phenyl, which is unsubstituted or substituted.

3. N-cyanopyridazinones according to claim 1, in which $R_2$ denotes hydrogen, $R_3$ denotes chlorine or bromine and $R_1$ denotes phenyl, which is substituted or unsubstituted.

4. N-cyanopyridazinones according to claim 1, in which $R_2$ denotes hydrogen, $R_3$ denotes chlorine and $R_1$ denotes phenyl.

5. Process for the preparation of N-cyanopyridazinones of the formula:

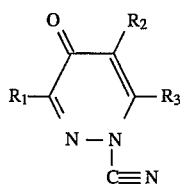

in which $R_2$ denotes hydrogen, Cl or Br, $R_1$ and $R_3$ are the same and each denotes Cl, Br or I or $R_1$ or $R_3$ denote Cl, Br, I, alkoxy having 1 to 8 carbon atoms, phenyl, which is unsubstituted or mono- or disubstituted by hydroxyl, halogen, cyano, nitro, amino, alkylamino having 1–4 C atoms, dialkylamino, each alkyl having 1–4 C atoms, straight-chain or branched alkyl having 1–10 C atoms being unsubstituted or mono-substituted by cyano or mono to trisubstituted by halogen; cycloalkyl having 5–7 C atoms, cycloalkoxy having 5–7 C atoms, phenyl, phenoxy, alkylthio or alkylsulfonyl having 1–4 C atoms; or trisubstituted by chlorine, which comprises:

reacting a hydroxypyridazine of the formula

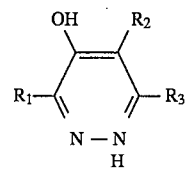

in which $R_1$, $R_2$ and $R_3$ have the above meaning, dissolved or suspended in a diluent, which is inert under reaction conditions, with an inorganic or organic base to yield the corresponding salt, reacting the salt with a cyanogen halide and isolating the N-cyanopyridazinone from the reaction mixture.

6. The process according to claim 5, which comprises employing cyanogen chloride or bromide as the cyanogen halide.

7. The process according to claim 5, wherein the base is sodium or potassium hydroxide or carbonate or a tertiary amine.

8. A herbicidal composition containing at least one N-cyanopyridazinone of the formula:

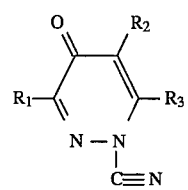

in which $R_2$ denotes hydrogen, Cl or Br, $R_1$ and $R_3$ are the same and each denote each Cl, Br or I or $R_1$ or $R_3$ denote Cl, Br, I, alkoxy having 1 to 8 carbon atoms, phenyl, which is unsubstituted or mono- or disubstituted by hydroxyl, halogen, cyano, nitro, amino, alkylamino having 1–4 C atoms, dialkylamino, each alkyl having 1–4 C atoms, straight-chain or branched alkyl having 1–10 C atoms being unsubstituted, mono-substituted by cyano or mono to trisubstituted by halogen; cycloalkyl having 5–7 C atoms, cycloalkoxy having 5–7 C atoms, phenyl, phenoxy, alkylthio or alkylsulfonyl having 1–4 C atoms; or trisubstituted by chlorine.

9. A method of controlling weeds which comprises applying the cyanopyridazinone of claim 1 to a locus containing weeds.

* * * * *